(12) United States Patent
Deal

(10) Patent No.: US 7,476,232 B2
(45) Date of Patent: Jan. 13, 2009

(54) ACCESS CATHETER HAVING DILATION CAPABILITY AND RELATED METHODS

(75) Inventor: Travis Deal, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 399 days.

(21) Appl. No.: 11/071,448

(22) Filed: Mar. 4, 2005

(65) Prior Publication Data

US 2006/0200184 A1    Sep. 7, 2006

(51) Int. Cl.
  *A61B 17/221* (2006.01)
  *A61M 29/00* (2006.01)
  *A61F 2/06* (2006.01)

(52) U.S. Cl. .............. 606/127; 606/191; 623/1.11; 623/1.22

(58) Field of Classification Search ......... 606/190–198, 606/200, 113, 110, 127; 604/103.08, 104–107, 604/198; 623/1.11
  See application file for complete search history.

(56) References Cited

U.S. PATENT DOCUMENTS

| | | | |
|---|---|---|---|
| 4,572,186 A | 2/1986 | Gould et al. | |
| 5,653,684 A * | 8/1997 | Laptewicz et al. | 604/22 |
| 5,935,139 A * | 8/1999 | Bates | 606/159 |
| 6,450,989 B2 * | 9/2002 | Dubrul et al. | 604/104 |
| 6,520,968 B2 | 2/2003 | Bates et al. | |
| 2002/0072708 A1 | 6/2002 | Ray et al. | |
| 2005/0256532 A1 * | 11/2005 | Nayak et al. | 606/151 |

FOREIGN PATENT DOCUMENTS

| | | |
|---|---|---|
| EP | 0 321 912 A1 | 6/1989 |
| GB | 1205743 | 9/1970 |
| WO | WO 01/60441 A1 | 8/2001 |
| WO | WO 2004/098697 A1 | 11/2004 |

* cited by examiner

*Primary Examiner*—Todd E Manahan
*Assistant Examiner*—Elizabeth Houston
(74) *Attorney, Agent, or Firm*—Finnegan, Henderson, Farabow, Garrett & Dunner LLP

(57) ABSTRACT

Various embodiments of a medical device having a dilation capability and related methods are disclosed. For example, the medical device may include a distal assembly having a radially expandable body defining a passageway therethrough, and a control member extending from the distal assembly to a proximal end of the device. Actuation of the control member may apply a compressive force to the body, causing the body to radially expand and a cross-sectional area of the passageway to increase.

53 Claims, 5 Drawing Sheets

ACCESS CATHETER HAVING DILATION CAPABILITY AND RELATED METHODS

FIELD OF THE INVENTION

The present invention relates generally to medical devices and related methods. More specifically, particular embodiments of the invention relate to an access catheter having a dilation capability for use in, for example, removal of stones or other objects from a body.

DESCRIPTION OF RELATED ART

Removal of stones or calculi from the urinary tract (e.g., bladder, ureter, or kidney) may involve insertion of a suitable retrieval device into the urinary tract, such as, for example, a retrieval basket to capture the stones or a laser or ultrasonic lithotripsy device to fragment the stones into smaller pieces that can be flushed out with urine or irrigation fluid. To gain access to a stone, a guidewire may be advanced through the urinary tract up to the location of the stone, and an access catheter may be advanced over the guidewire to provide an access path for a suitable retrieval device to access the stone. A suitable retrieval device then may be inserted through the access catheter to retrieve the stone.

Due to the safety concerns associated with manipulation of the retrieval device in the narrow urinary tract, it is often necessary to dilate at least a portion of the tract in the vicinity of the stone location to minimize the potential damage to the tract lining and to permit greater device maneuverability for stone removal.

In some cases, access sheaths are placed in the urinary tract after a series of dilators have been inserted. Alternatively, a balloon catheter is used to dilate the urinary tract. These devices, however, may limit the space in the access catheter for the retrieval device, which may require insertion of additional devices to gain sufficient access to the stones. Moreover, insertion and removal of various dilators and access sheaths may prolong the duration of the procedure and thereby cause greater trauma to the patient.

SUMMARY OF THE INVENTION

Therefore, an exemplary embodiment of the invention may provide an access catheter having an integrated dilation mechanism, that may provide sufficient access to the stones during the stone retrieving procedure without requiring any additional dilation device.

To attain the advantages and in accordance with the purpose of the invention, as embodied and broadly described herein, one aspect of the invention may provide a medical device comprising a distal assembly having a radially expandable body defining a passageway therethrough, and a control member extending from the distal assembly to a proximal end of the device. Actuation of the control member may apply a compressive force to the body causing the body to radially expand and a cross-sectional area of the passageway to increase.

In some exemplary aspects of the invention, the body may comprise at least two helical coils interwoven with each other. At least one of the two helical coils may be made of a plastic material. One of the at least two helical coils may be wound in a clockwise direction and the other of the at least two helical coils may be wound in a counterclockwise direction.

According to another exemplary aspect, at least one of a proximal end and a distal end of the body may be connected to the control member, wherein actuation of the control member causes the proximal and distal ends of the body to move closer to each other to expand the body. The device may comprise a handle coupled to a proximal end of the control member.

In an aspect, the control member may comprise a pusher configured to impart the compressive force on the body along a longitudinal axis of the body. The pusher may be a flexible tube. The control member may also include a wire slidable within the tube. In another aspect, the control member includes at least one wire attached to a distal end of the body. The at least one wire may include two wires.

In still another aspect of the invention, the device may comprises a flexible sheath covering at least a portion of the distal assembly.

In yet still another aspect of the invention, the distal assembly may be detachable from the control member.

Some exemplary aspects of the invention may provide a medical device comprising a distal assembly comprising a tubular body having at least two helical bodies interwoven with each other, and a control member extending from the distal assembly to a proximal end of the device. The control member may include at least one tube proximate a proximal end of the at least two helical bodies and at least one elongate member slidable with the tube and attached to a distal end of the at least two helical bodies. Actuation of the control member applies a compressive force to the tubular body causing the tubular body to radially expand.

In another aspect, the tubular body may define a passageway therethrough between a proximal end and a distal end of the tubular body. A cross-sectional area of the passageway may increase as the tubular body expands radially.

In still another aspect of the invention, at least one of the two helical bodies may be made of a plastic material. In yet still another aspects, one of the at least two helical bodies may be wound in a clockwise direction and the other of the at least two helical bodies may be wound in a counterclockwise direction.

In various aspects, the device may comprise a handle coupled to a proximal end of the control member.

According to some aspects of the invention, actuation of the control member may cause the proximal and distal ends of the tubular body to move closer to each other to expand the tubular body. For example, the at least one elongate member may be configured to impart the compressive force on the tubular body along a longitudinal axis of the tubular body. Alternatively or additionally, the at least one tube may be configured to impart the compressive force on the tubular body along a longitudinal axis of the tubular body. Axial movement of the elongate member relative to the tube may apply the compressive force to the tubular body.

In another aspect, the device may further comprise a flexible sheath covering at least a portion of the distal assembly.

In an aspect, the elongate member may be a wire. In some exemplary embodiments, the at least one elongate member may include two wires. In another aspect, the at least one tube may include two tubes.

In still another aspect of the invention, the distal assembly may be detachable from the control member.

According to another aspect of the invention, a method of performing a medical procedure may be provided. For example, the method may comprise providing a first medical device comprising a distal assembly having a radially expandable body defining a passageway therethrough, inserting the distal assembly into a body lumen, and applying a compressive force to the body to radially expand the body and dilate the body lumen. In some exemplary embodiments, expanding the body may increase a cross-sectional area of the passageway inside the tubular body.

In an aspect, the method may further comprise inserting a second medical device through the passageway of the first medical device.

In another aspect of the invention, the compressive force may be applied along a longitudinal axis of the body.

According to still another aspect, the body may comprise at least two helical coils interwoven with each other. For example, one of the at least two helical coils may be wound in a clockwise direction, and the other of the at least two helical coils may be wound in a counterclockwise direction. In some exemplary aspects, the first medical device may comprise a control member configured to impart the compressive force on the at least two helical coils along a longitudinal axis of the body.

In another aspect, at least a portion of the distal assembly includes a flexible sheath.

Some aspects of the invention may further comprise detaching the body from the remainder of the first medical device and withdrawing the first medical device from the body lumen while leaving the body in the body lumen.

In another aspect, inserting the distal assembly may comprise positioning the distal assembly proximate a bodily object located in the lumen. In still another aspect, the method may further comprise, after applying the compressive force, performing an operation on the bodily object. The operation may include at least one of breaking apart the bodily object and retrieving the bodily object from the body lumen. In some exemplary embodiments, the bodily object may be a stone in the urinary tract.

According to some aspects of the invention, the first medical device may comprise a control member extending from the distal assembly to a proximal end of the device, where actuation of the control member may apply the compressive force to the body. For example, at least one of a proximal end and a distal end of the body may be connected to the control member, where actuation of the control member may apply the compressive force to the body, causing the proximal and distal ends of the body to move closer to each other to expand the body.

In various aspects of the invention, the control member may include at least one tube proximate a proximal end of the body and at least one elongate member slidable with the tube and attached to a distal end of the body. The at least one elongate member may be configured to impart the compressive force on the body along a longitudinal axis of the body. Alternatively or additionally, the at least one tube may be configured to impart the compressive force on the tubular body along a longitudinal axis of the body. For example, axial movement of the elongate member relative to the tube may apply the compressive force to the body.

In an aspect, the elongate member may be a wire. In another aspect, the elongate member may include two wires, and the at least one tube may include two tubes. In some exemplary embodiments, the first medical device further comprises a handle coupled to a proximal end of the control member.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate an exemplary embodiment of the invention and together with the description, serve to explain the principles of the invention. In the drawings.

DESCRIPTION OF THE EMBODIMENTS

Reference will now be made in detail to the exemplary embodiments consistent with the present invention, examples of which are illustrated in the accompanying drawings. Wherever possible, the same reference numbers will be used throughout the drawings to refer to the same or like parts.

Figure 1:
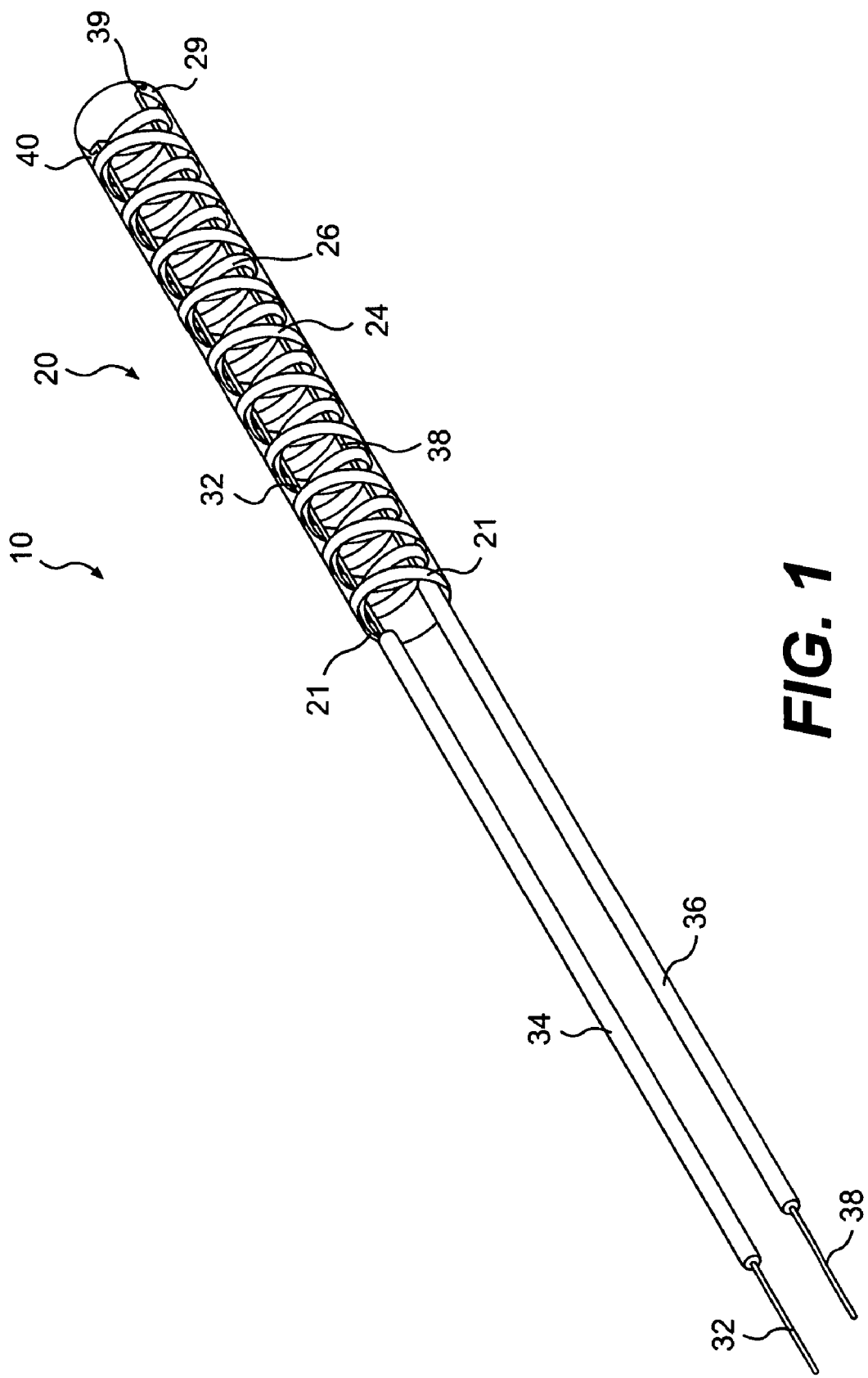
FIG. 1 is a partial schematic view of an access catheter having a dilation mechanism, according to an exemplary embodiment of the invention.

FIG. 1 illustrates a distal portion of a medical device, such as an access catheter 10 having a dilation mechanism for dilating, for example, a portion of the urinary tract (e.g., ureter), according to an exemplary embodiment of the invention. While the invention will be described in connection with a particular urology application (i.e., stone removal in the urinary tract), embodiments of the invention may be applied to, or used in connection with, other numerous medical and non-medical applications. For example, embodiments of the present invention may be used to dilate, expand, and/or repair occluded blood vessels, gastrointestinal tracts, or other body lumens or cavities. Some embodiments of the present invention may also be used to deploy or remove medical stents. Moreover, the exemplary dilation mechanism of the present invention may be used in combination with numerous other medical devices including, but not limited to: other dilation devices, such as, for example, balloons or other mechanical expanders; sphincterotome devices used in, for example, endoscopic retrograde cholangio pancreatography (ERCP); and tissue retrieval devices, such as, for example, forceps, baskets, snares, needles, or pincers.

As shown in FIG. 1, the distal portion of the access catheter 10 may include a generally tubular body 20. The tubular body 20 may be coupled to a suitable actuation member (not shown) located at the proximal end of the catheter 10 and connected to the body 20 via a suitable control mechanism. The actuation member can be any suitable handle known in the art so that, as will be described in detail herein, actuation of the actuation member may cause the tubular body 20 to radially expand so as to dilate a body lumen or cavity. Alternatively, pull wires 32, 38 and pushers 34, 36 (to be described herein) may simply extend to the proximal end of the catheter 10, and their free proximal ends may be manipulated by the user to operate the catheter 10.

The tubular body 20 may include a flexible tubular sheath 40 made of a suitable biocompatible material, such as, for example, silicon, Teflon, PTFE, or any other suitable material known in the art. At least a portion of the tubular body 20 may be coated with a lubricating material, such as, for example, liquid silicon, to facilitate the axial movement of the tubular body 20.

The tubular body 20 may include two or more helical bodies 24, 26, such as, for example, helical coils, interwoven or braided into a tubular mesh. The rotational direction of each of the helical bodies 24, 26 may be opposite from one another such that, when the helical bodies 24, 26 are axially compressed along its longitudinal axis, the helical bodies 24, 26 of the tubular body 20 may radially expand through the interaction between the helical bodies 24, 26 (e.g., similar to a Chinese finger trap). For example, at least one of the helical bodies 24, 26 may be wound in a clockwise direction, while the other of the helical bodies 24, 26 is wound in a counterclockwise direction. In this particular arrangement, when an axial compressive force is applied to the helical bodies 24, 26 along their longitudinal axis, the helical bodies 24, 26 transfer at least a portion of the applied compressive force against each other, whose resultant force is directed radially outwardly.

The helical body 24, 26 may be sufficiently flexible to traverse through a tortuous body lumen, yet stiff enough to dilate the lumen being dilated (e.g., ureter). For that purpose, the helical body 24, 26 may be formed of a semi-rigid plastic material. Alternatively or additionally, at least a portion of the helical body 24, 26 may be formed of a flexible metal, such as, for example, stainless steel. In some exemplary embodiments, the helical body 24, 26 may be made of a memory material, such as, nitinol (i.e., nickel-titanium alloy).

Figure 4:
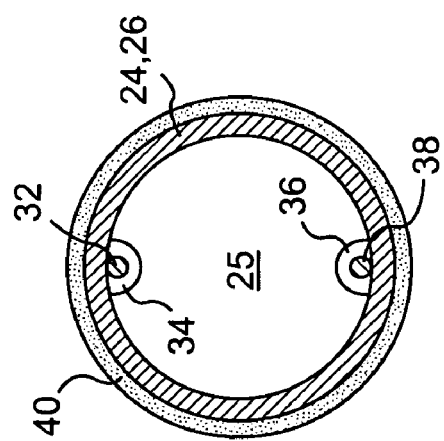
FIG. 4 is an axial cross-sectional view of the access catheter shown in FIG. 3, along IV-IV plane.
Figure 3:
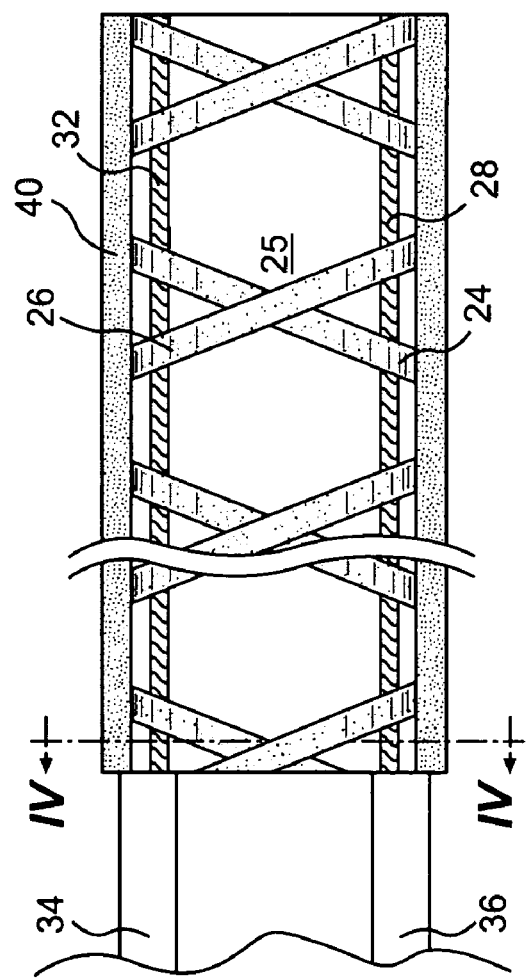
FIG. 3 is a partial cross-sectional view of the access catheter shown in FIG. 1, illustrating an unexpanded state.

The ratio of expansion of the helical bodies 24, 26 from an unexpanded configuration (shown in FIGS. 3 and 4) to an expanded configuration (shown in FIGS. 5 and 6) may depend upon, among other things, the number of helical bodies 24, 26, the spiral angle of the helical bodies 24, 26, material properties of the helical bodies 24, 26, and the magnitude of the applied axial compressive force.

Figure 2:
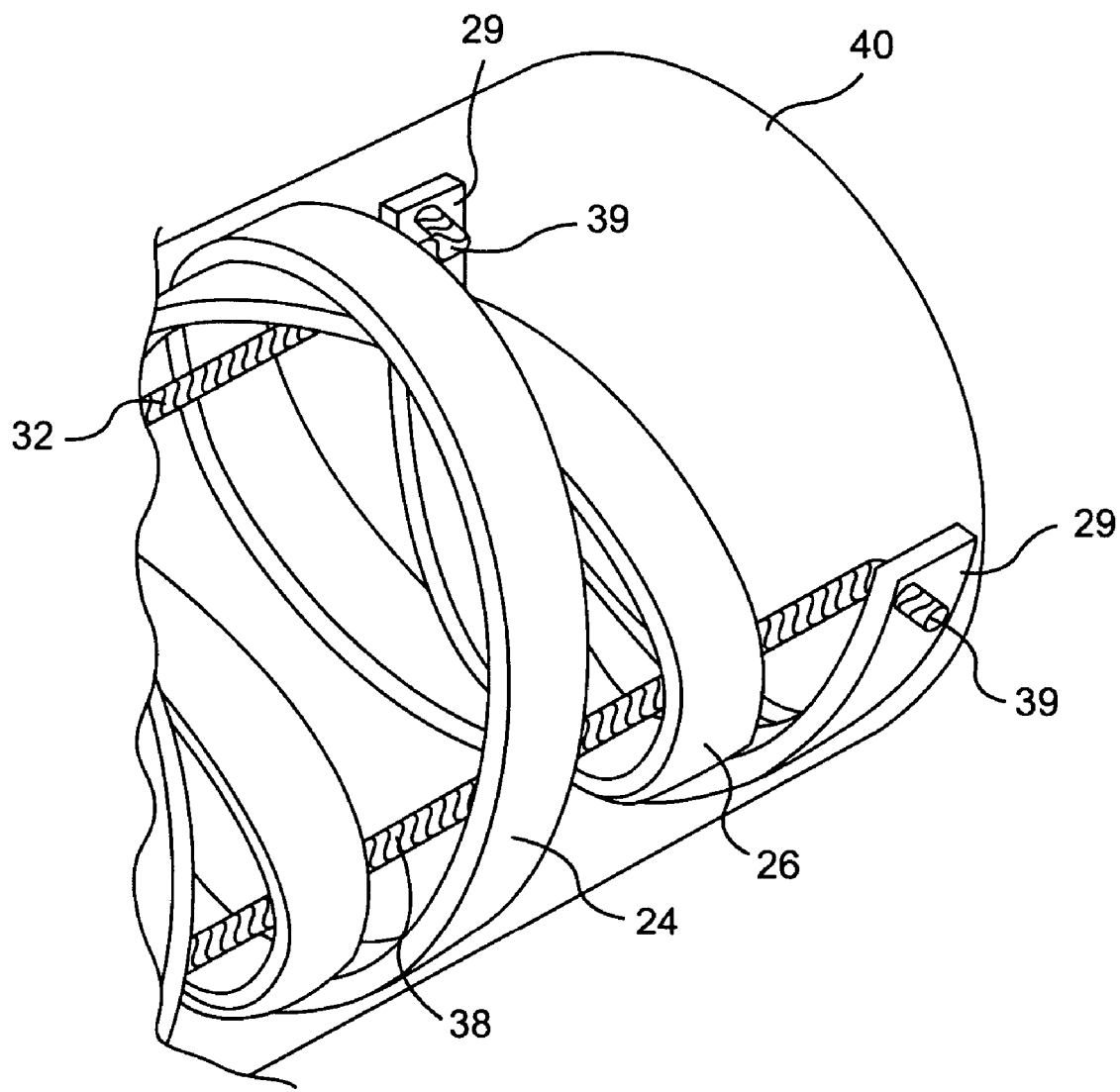
FIG. 2 is an exploded schematic view of a distal portion of the access catheter shown in FIG. 1.

To apply the compressive force, a suitable control member, such as one or more pull wires, may extend from the actuation member (which may be outside of a patient) to the helical bodies 24, 26. In the exemplary embodiment shown in FIGS. 1 and 2, the control member includes a pair of pull wires 32, 38, and the distal ends 29 of the helical bodies 24, 26 are fixedly connected to the distal ends 39 of the pull wires 32, 38, respectively, while the remainder of the helical bodies 24, 26, including their proximal ends 21, slide relative to the pull wires 32, 38. As best shown in FIG. 2, distal end 39 of pull wire 32 may be coupled to distal end 29 of helical body 26 and uncoupled to distal end 29 of helical body 24. while distal end 39 or null wire 38 may be coupled to distal end 29 of helical body 24 and uncoupled to distal end 29 of helical body 26. Each of the distalmost ends 39 of the pull wires 32, 38 may include a bent portion that may extend through a bore formed in the distal end 29 of each helical body 24, 26 to connect to the helical body 24, 26. Other suitable connection mechanisms known in the art, such as, for example, crimping, soldering, welding, fusing, and adhesive, may be used alternatively or additionally.

The control member may also include a pair of pushers 34, 36 configured to impart an axial compressive force against the proximal ends 21 of the helical bodies 24, 26. In an exemplary embodiment, each of the pushers 34, 36 may form a hollow body defining a passageway for a corresponding pull wire 32, 38 to slidably pass through, as shown in FIG. 1. The pushers 34, 36 may be flexible enough to pass through a tortuous body lumen or cavity, yet sufficiently stiff to impart sufficient axial compressive force against the helical bodies 24, 26 without collapsing or bending, so as to expand the helical bodies 24, 26. In an exemplary embodiment, each of the pushers 34, 36 may be fixedly connected to the proximal end 21 of each helical body 24, 26.

Figure 6:
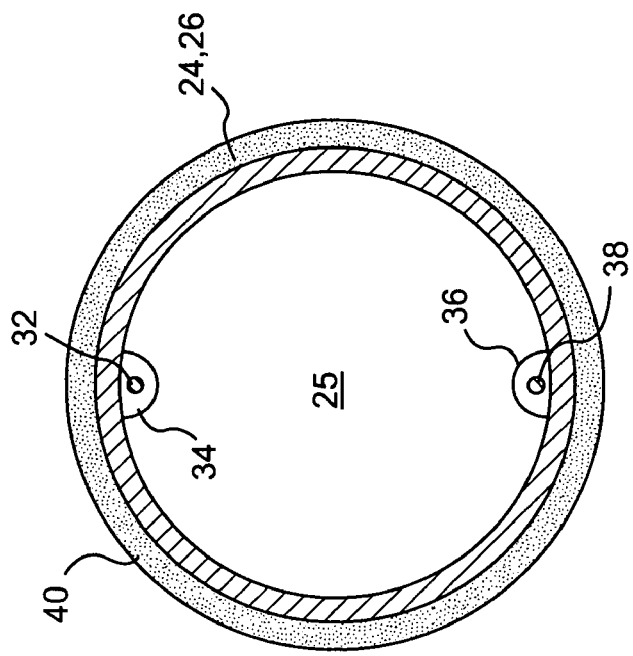
FIG. 6 is an axial cross-sectional view of the expanding access catheter shown in FIG. 5, along VI-VI plane.
Figure 5:
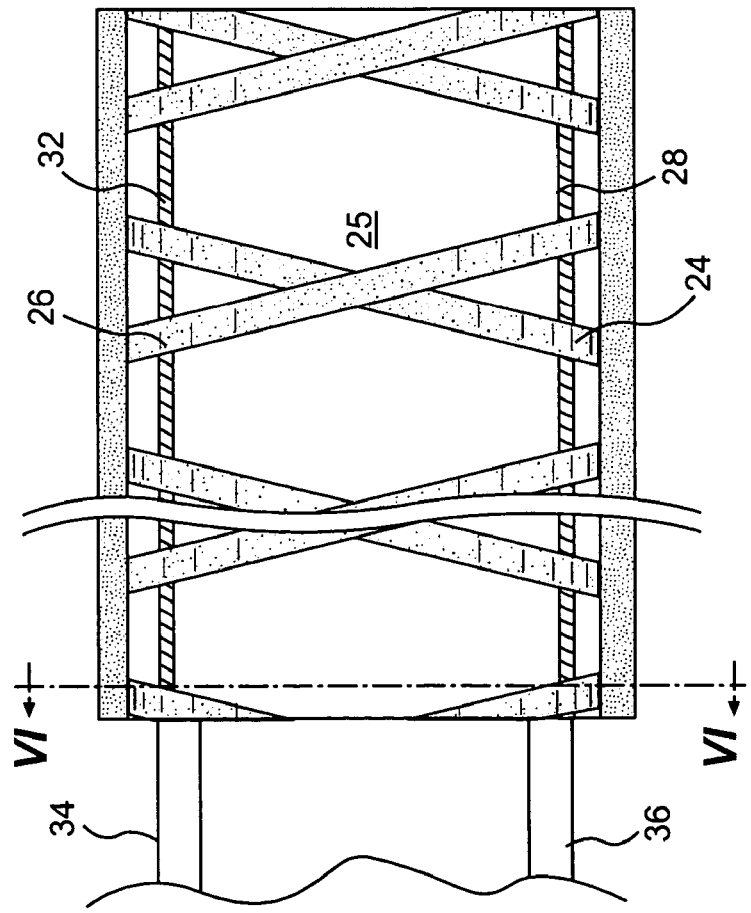
FIG. 5 is a partial cross-sectional view of the access catheter shown in FIG. 1, illustrating an expanded state.

In operation, an operator may push the pushers 34, 36 relative to the pull wires 32, 38 so as to impart an axial compressive force against the proximal ends 21 of the helical bodies 24, 26. Alternatively or additionally, the operator may pull the pull wires 32, 38 relative to the pushers 34, 36 to impart an axial compressive force against the distal ends 29 of the helical bodies 24, 26. Upon actuation of the axial compressive force, the helical bodies 24, 26 may expand radially, as shown in FIGS. 5 and 6, with a substantial increase in the internal space 25 within the helical bodies, which may provide sufficient access space for a stone retrieval device to maneuver to and/or around a stone.

In an alternative exemplary embodiment, the distal ends 29 of the helical bodies 24, 26 may be connected to a coupling member (not shown), and the coupling member may be connected to a suitable control member, eliminating the need for multiple control members.

The pull wires 32, 38 and the pushers 34, 36 shown and described in FIGS. 1-6 are exemplary only. Other control and/or actuation mechanisms known in the art that can actuate the helical bodies 24, 26 may be used alternatively or additionally.

According to another exemplary embodiment, instead of applying an axial compressive force to the helical bodies 24, 26, the helical bodies 24, 26 may be biased to expand at a stress-free, resting state. For example, at least one of the ends 21, 29 of the helical bodies 24, 26 may be pulled/pushed axially away from one another, so that the helical bodies 24, 26 may collapse from the normal expanded configuration to a collapsed configuration. The biased helical bodies 24, 26 may then be inserted into a patient in this collapsed configuration, and a suitable actuation mechanism may be used to gradually release the applied force to allow the helical bodies 24, 26 to return to its normal expanded configuration to dilate the lumen. In some exemplary embodiments, the suitable actuation mechanism may include a locking mechanism to lock the helical bodies 24, 26 in the collapsed state during insertion into a patient.

According to still another exemplary embodiment of the invention, the tubular body 20 may be detachable from the actuation mechanism and the control member, so as to permit the tubular body 20 to remain inside a patient even after completion of a procedure. Thus, in some exemplary embodiments, the tubular body 20 may be used as a stent or an independent expander.

The operation of the device 10, according to an exemplary embodiment of the invention, will be described in detail with reference to FIGS. 7-9. While operational aspects of the invention will be described in connection with a particular stone removal procedure, embodiments of the invention may be applied to other suitable medical procedures, or used in connection with any other suitable medical devices, without departing from the scope of the invention.

Figure 7:
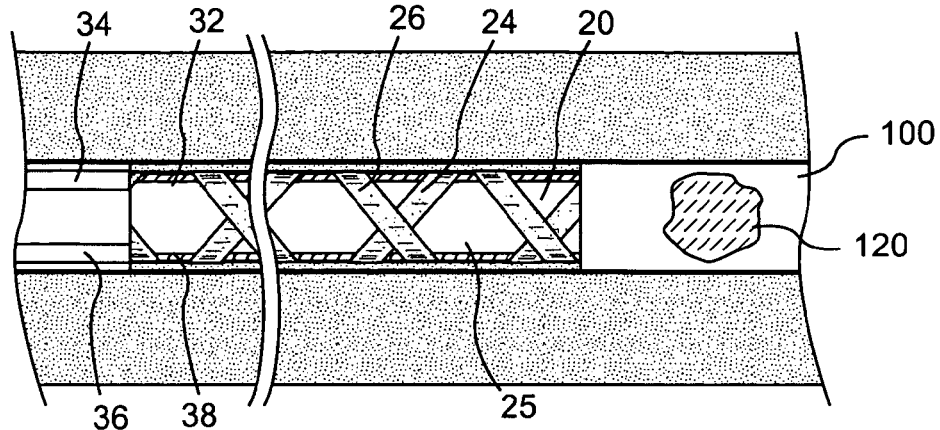
FIGS. 7-9 are schematics illustrating an exemplary method of using the access catheter of FIG. 1, according to an embodiment of the invention.
Figure 8:
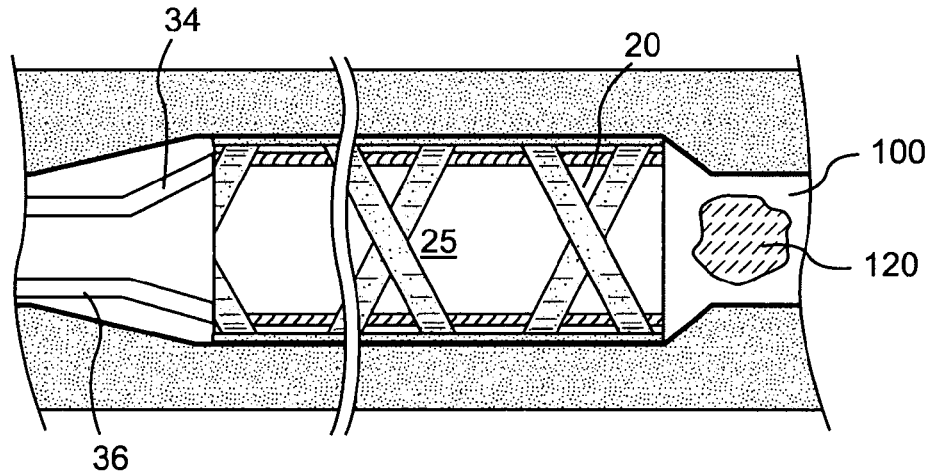

As shown in FIG. 7, the device 10 may be inserted over a suitable guidewire (not shown) into a ureter 100 in an unexpanded configuration to position the tubular body 20 near a stone 120. Once the distal end of the tubular body 20 is properly positioned, the actuation member may be actuated to apply an axial compressive force (e.g., by pushing the pushers 34, 36 distally and/or pulling the pull wires 32, 38 proximally), causing the tubular body 20 to radially expand and thereby dilating the ureter 100, as shown in FIG. 8. If the tubular body 20 is biased to expand in a resting state, and the device 10 is inserted into the ureter 100 in a collapsed configuration, the actuation member may be actuated to gradually release the applied force to allow the tubular body 20 to expand to its normal expanded configuration.

Figure 9:
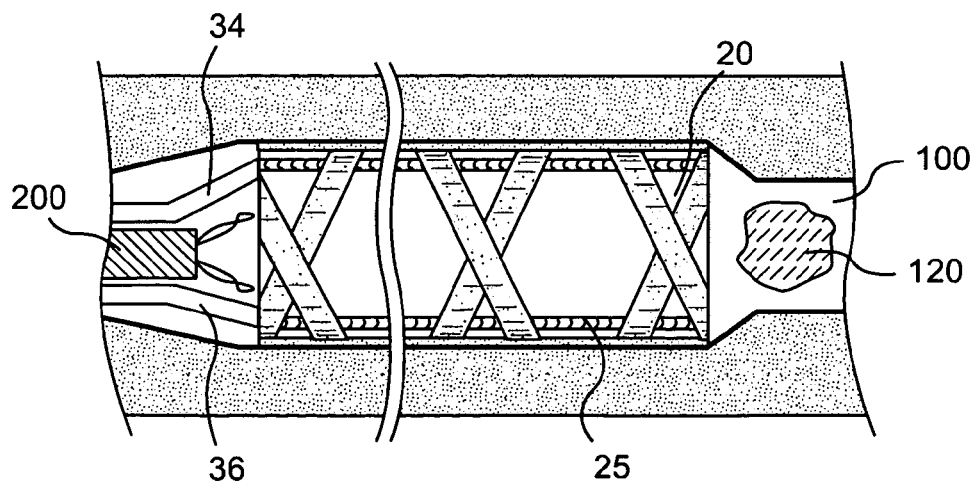

After the ureter 100 is sufficiently dilated in the vicinity of the stone 120, a stone retrieving device, such as a forceps 200, a stone basket, or a snare may be inserted through the expanded space 25 of the tubular body 20 to retrieve the stone 120, as shown in FIG. 9. In various other exemplary embodiments, other types of stone retrieving devices or therapeutic or diagnostic devices, such as, for example, laser or ultrasonic lithotripsy devices, may be utilized alternatively or additionally.

After the procedure, the stone retrieving device or any other device that has been inserted into the tubular body 20 may be removed, and the actuation member may be manipulated to release the axial compressive force applied to the tubular body 20 (e.g., moving the pushers 34, 36 proximally and/or moving the pull wires 32, 38 distally), causing the tubular body 20 to collapse into the unexpanded configuration. In this unexpanded configuration, the access catheter 10 including the tubular body 20 may be removed from the ureter 100.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a distal assembly having a radially expandable body defining a passageway therethrough; and
   a control member extending from the distal assembly to a proximal end of the device, the control member including a plurality of wires coupled to a distal end of the body and extending to the proximal end of the device and a plurality of rods coupled to a proximal end of the body and extending to the proximal end of the device, wherein the plurality of wires comprise two wires, the plurality of rods comprise two rods, and the body comprises at least a first helical coil and a second helical coil interwoven with each other, the first helical coil being wound in a clockwise direction and the second helical coil being wound in a counterclockwise direction, one wire of the two wires being coupled to a distal end of the first helical coil and uncoupled to a distal end of the second helical coil, a distal end of one rod of the two rods being coupled to a proximal end of the first helical coil and uncoupled to a proximal end of the second helical coil,
   wherein actuation of the control member applies a compressive force to the body causing the body to radially expand and a cross-sectional area of the passageway to increase substantially uniformly from the proximal end of the body to the distal end of the body.

2. The device of claim 1, wherein the body consists essentially of two helical coils circumferentially disposed about the passageway.

3. The device of claim 1, wherein actuation of the control member causes the proximal and distal ends of the body to move closer to each other to expand the body.

4. The device of claim 1, wherein the plurality of rods and the plurality of wires are configured to impart the compressive force on the body along a longitudinal axis of the body.

5. The device of claim 4, wherein the plurality of rods are flexible tubes.

6. The device of claim 5, wherein each wire of the plurality of wires passes through a tube of the flexible tubes.

7. The device of claim 6, wherein longitudinal axes of each tube of the flexible tubes are displaced from each other.

8. The device of claim 1, further comprising a flexible sheath covering at least a portion of the distal assembly.

9. The device of claim 1, wherein the distal assembly is detachable from the control member.

10. The device of claim 1, wherein each wire of the plurality of wires is connected to the distal end of the body, and each rod of the plurality of rods is connected to the proximal end of the body.

11. The device of claim 1, wherein actuation of the control member causes the body to radially expand and the cross-sectional area of the passageway to increase substantially uniformly along an entire length of the body.

12. A medical device comprising:
    a distal assembly comprising a tubular body including a first part and a second part extending along a common longitudinal axis; and
    a control member extending from the distal assembly to a proximal end of the device, the control member including a first wire slidably disposed through a first tube and a second wire slidably disposed through a second tube, a distal end of the first wire being coupled to a distal end of the first part and uncoupled to a distal end of the second part, a distal end of the first tube being coupled to a proximal end of the first part, a distal end of the second wire being coupled to a distal end of the second part and uncoupled to a distal end of the first part, a distal end of the second tube being coupled to a proximal end of the second part,
    wherein actuation of the control member applies a compressive force to the tubular body causing the tubular body to radially expand.

13. The device of claim 12, wherein the tubular body defines a passageway extending longitudinally from a first end of the tubular body to a second end of the tubular body, wherein a cross-sectional area of the passageway increases substantially uniformly from the first end to the second end as the tubular body expands radially.

14. The device of claim 12, wherein at least one of the first part and the second part is made of a plastic material.

15. The device of claim 12, wherein one of the first part and the second part is wound in a clockwise direction and the other is wound in a counterclockwise direction.

16. The device of claim 12, wherein actuation of the control member causes the first part and the second part of the tubular body to move closer to each other to expand the tubular body.

17. The device of claim 12, further comprising a handle coupled to a proximal end of the control member.

18. The device of claim 12, wherein at least one pair of the first wire and the first tube, and the second wire and the second tube, are configured to impart the compressive force on the tubular body.

19. The device of claim 12, wherein the control member consists essentially of the first wire slidably disposed through the first tube and the second wire slidably disposed through the second tube.

20. The device of claim 12, further comprising a flexible sheath covering at least a portion of the distal assembly.

21. The device of claim 12, wherein the tubular body consists essentially of the first part and the second part.

22. The device of claim 12, wherein axial movement of the first wire and the second wire relative to the first tube and the second tube applies the compressive force to the tubular body.

23. The device of claim 12, wherein the distal assembly is detachable from the control member.

24. The device of claim 12, wherein the first wire and the first tube are uncoupled to the second part, and the second wire and the second tube are uncoupled to the first part.

25. The device of claim 12, wherein longitudinal axes of each tube of the at least two tubes are displaced from each other and the common longitudinal axis.

26. The device of claim 12, wherein actuation of the control member causes the tubular body to expand substantially uniformly along an entire length of the body.

27. The device of claim 26, wherein a cross-section area of the body in a direction perpendicular to the common longitudinal axis is substantially uniform along the entire length of the body, after the tubular body expands.

28. A method of performing a medical procedure, comprising:
   providing a first medical device comprising a distal assembly having a radially expandable body defining a passageway therethrough, the first medical device including a control member, the control member including a plurality of elongate members coupled to a distal end of the body and extending to the proximal end of the first medical device and a plurality of tubes coupled to a proximal end of the body and extending to the proximal end of the first medical device;
   inserting the distal assembly into a body lumen; and
   applying a compressive force to the body by the plurality of elongate members and the plurality of tubes to radially expand the body and dilate the body lumen,
   wherein expanding the body increases a cross-sectional area of the passageway substantially uniformly from the proximal end of the body to the distal end of the body.

29. The method of claim 28, further comprising inserting a second medical device through the passageway of the first medical device.

30. The method of claim 28, wherein the compressive force is applied along a longitudinal axis of the body.

31. The method of claim 28, wherein the body comprises at least two helical coils interwoven with each other.

32. The method of claim 31, wherein one of the at least two helical coils is wound in a clockwise direction and the other of the at least two helical coils is wound in a counterclockwise direction.

33. The method of claim 31, wherein the first medical device includes a same number of helical coils, elongate members and tubes, and each elongate member and each wire is coupled to only one helical coil.

34. The method of claim 28, wherein at least a portion of the distal assembly includes a flexible sheath.

35. The method of claim 28, further comprising detaching the body from the remainder of the first medical device and withdrawing the first medical device while leaving the body in the body lumen.

36. The method of claim 28, wherein inserting the distal assembly comprises positioning the distal assembly proximate a bodily object located in the lumen.

37. The method of claim 36, further comprising, after applying the compressive force, performing an operation on the bodily object.

38. The method of claim 37, wherein the operation includes retrieving the bodily object from the body lumen.

39. The method of claim 36, wherein the bodily object is a stone in the urinary tract.

40. The method of claim 28, wherein actuation of the control member applies the compressive force to the body.

41. The method of claim 28, wherein actuation of the control member causes the proximal and distal ends of the body to move closer to each other to expand the body.

42. The method of claim 28, wherein each elongate member of the plurality of elongate members is slidably disposed within a tube of the plurality of tubes.

43. The method of claim 42, wherein each elongate member is a wire.

44. The method of claim 28, wherein the at least two elongate members consists essentially of two elongate members.

45. The method of claim 28, wherein the at least two tubes consists essentially of two tubes.

46. The method of claim 28, wherein axial movement of the at least two elongate members relative to the at least two tubes applies the compressive force to the body.

47. The method of claim 28, wherein the first medical device further comprises a handle coupled to a proximal end of the control member.

48. The method of claim 28, wherein expanding the body increases the cross-sectional area of the passageway substantially uniformly along an entire length of the body.

49. A medical device comprising:
   a distal assembly comprising a tubular body having at least a first part and a second part circumferentially disposed about a central passageway and extending from a first end to a second end; and
   a control member extending from the distal assembly to a proximal end of the device, the control member including a first tube with a first wire slidably disposed therein and a second tube with a second wire slidably disposed therein, a distal end of the first tube being coupled to the first end of the first part and uncoupled to the first end of the second part, a distal end of the first wire being coupled to a second end of the first part, a distal end of the second tube being coupled to the first end of the second part and uncoupled to the first end of the first part, a distal end of the second wire being coupled to a second end of the second part,
   wherein actuation of the control member causes the central passageway to radially expand substantially uniformly from the first end to the second end.

50. The device of claim 49, wherein the first part extends helically from the first end to the second end in a clockwise direction and the second part extends helically from the first end to the second end in a counterclockwise direction.

51. The device of claim 49, wherein actuation of the control member causes relative displacement between the first tube and the first wire, and the second tube and the second wire, causing the first and second ends of the body to move closer to each other.

52. The device of claim 49, wherein the first wire and the first tube are uncoupled to the second part and the second wire and the second tube are uncoupled to the first part.

53. The device of claim 49, wherein longitudinal axes of the first tube and the second tube are displaced from each other and longitudinal axes of the first wire and the second wire are displaced from each other.

* * * * *